US010240121B2

(12) United States Patent
Gevaert et al.

(10) Patent No.: US 10,240,121 B2
(45) Date of Patent: Mar. 26, 2019

(54) BIOREACTOR SYSTEM

(75) Inventors: Matthew R. Gevaert, Greenville, SC (US); David E. Orr, Piedmont, SC (US); Margaret Rebecca Widener, Central, SC (US)

(73) Assignee: KIYATEC INC., Pendleton, SC (US)

( * ) Notice: Subject to any disclaimer, the term of this patent is extended or adjusted under 35 U.S.C. 154(b) by 0 days.

(21) Appl. No.: 13/817,636

(22) PCT Filed: Aug. 16, 2011

(86) PCT No.: PCT/US2011/047933
§ 371 (c)(1),
(2), (4) Date: Aug. 8, 2013

(87) PCT Pub. No.: WO2012/024304
PCT Pub. Date: Feb. 23, 2012

(65) Prior Publication Data
US 2013/0309771 A1    Nov. 21, 2013

Related U.S. Application Data

(60) Provisional application No. 61/374,000, filed on Aug. 16, 2010.

(51) Int. Cl.
*C12N 5/00* (2006.01)
*C12M 3/00* (2006.01)
*C12M 1/12* (2006.01)

(52) U.S. Cl.
CPC .......... *C12N 5/0062* (2013.01); *C12M 21/08* (2013.01); *C12M 23/44* (2013.01); *C12M 25/14* (2013.01)

(58) Field of Classification Search
CPC ....... A61K 9/0065; A61L 15/18; A61L 15/28; A61L 15/32; A61L 15/40; A61L 15/46; A61L 2300/102; A61L 2300/404; A61L 2300/63; B01J 20/26; B32B 27/18; B32B 9/02; B81B 2201/058; B81C 1/00119; C08F 220/06; C08F 220/56; C08F 251/00; C08F 289/00; C08F 2/44
USPC ........... 422/503; 428/304.4, 311.11, 311.71, 428/312.2, 312.6; 435/309.1
IPC .............. A61K 9/00; A61L 15/28,15/32; B01J 20/24, 20/26; C08K 9/00, 9/08
See application file for complete search history.

(56) References Cited

U.S. PATENT DOCUMENTS

| | | | | |
|---|---|---|---|---|
| 6,323,022 | B1 * | 11/2001 | Chang et al. | 435/286.5 |
| 6,991,652 | B2 * | 1/2006 | Burg | 623/8 |
| 8,864,844 | B2 * | 10/2014 | Ratcliffe | A61L 27/3633 424/424 |
| 2002/0022883 | A1 | 2/2002 | Burg et al. | |
| 2007/0238169 | A1 | 10/2007 | Abilez et al. | |
| 2008/0057571 | A1 | 3/2008 | Loboa et al. | |
| 2008/0293135 | A1 * | 11/2008 | Orr et al. | 435/357 |
| 2009/0215176 | A1 | 8/2009 | Orr | |

FOREIGN PATENT DOCUMENTS

| | | | |
|---|---|---|---|
| WO | 03093408 | A1 | 11/2003 |
| WO | 2007021919 | A1 | 2/2007 |
| WO | 2008060541 | A2 | 5/2008 |
| WO | 2009108654 | A2 | 9/2009 |
| WO | 2009116951 | A2 | 9/2009 |

OTHER PUBLICATIONS

Altmann et al. 2009. The famous versus the inconvenient—or the dawn and the rise of 3D-culture systems. World J Stem Cells 2009 vol. 1, No. 1, pp. 43-48.*
Whitford et al (2009. Interest in Hollow-Fiber Perfusion Bioreactors is Growing. Bioprocess International, Oct. 2009, pp. 54-63.*
Freed et al. 1998.Culture of organized cell communities. Advanced Drug Delivery Reviews, vol. 33, pp. 15-30.*
Moutos et al 2008. Composite scaffolds for cartilage tissue engineering. Biorheology, vol. 45, pp. 501-512.*
Marijnissen et al. 2002. Alginate as a chondrocyte-delivery substance in combination with a non-woven scaffold for cartilage tissue engineering. Biomaterials vol. 23, pp. 1511-1517.*
International Search Report and Written Opinion for PCT/US2011/047933, dated Apr. 9, 2012, 6.
European Search Report for European Patent Application No. 11818667.5, dated Jun. 21, 2017, 10.
Kiyatec, "Introducing 3DKUBE", Retrieved from the Internet: https://www.youtube.com/watch?v=TEQGy9DauXE [retrieved on May 30, 2017], Dec. 1, 2010, 1-5.

* cited by examiner

*Primary Examiner* — Louise W Humphrey
*Assistant Examiner* — Stephen A Perkins
(74) *Attorney, Agent, or Firm* — F. Brent Nix, Esq.; Johnson, Marcou & Isaacs, LLC

(57) ABSTRACT

Disclosed herein are bioreactor systems and methods of utilizing said systems.

18 Claims, 7 Drawing Sheets

BIOREACTOR SYSTEM

CROSS-REFERENCE TO RELATED APPLICATIONS

The present application is a U.S. National Phase Application of International Application No. PCT/US2011/047933, filed Aug. 16, 2011, which claims the benefit of U.S. Provisional Application No. 61/374,000, filed Aug. 16, 2010, all of which applications are incorporated herein fully by this reference.

BACKGROUND OF THE INVENTION

The ability to culture in vitro viable three-dimensional cellular constructs that mimic natural tissue has proven very challenging. One of the most difficult of the many problems faced by researchers is that there are multiple dynamic biochemical and mechanical interactions that take place between and among cells in vivo, many of which have yet to be fully understood, and yet the complicated in vivo system must be accurately modeled if successful development of engineered tissues in vitro is to be accomplished. The ideal in vitro system should accurately model the mechanical environment as well as the essential cellular interactions found during in vivo development while providing purity of the desired product construct so as to enable utilization of the product, for instance as transplantable tissue.

Many existing culture systems are simple well plate designs that are static in nature and do not allow for manipulation of the local environment beyond the gross chemical inputs to the system. As such, the development of more dynamic culture systems has become of interest, because it introduces the possibility of advantageously changing the local environment over the course of a cell culture experiment. However, known dynamic systems have not been widely implemented in the field of cell culture, as they are labor intensive, cost prohibitive, have configurations which limit their experimental flexibility and lack inter- and intra-lab comparability because there is no universal standard procedure.

In another aspect, there are many advantages to culturing cells in 3D (as opposed to historic 2D cell culture) that are being increasingly appreciated with a societal focus on higher and higher fidelity in vitro models of in vivo human physiology. One of these many advantages relates to the cultured cells' phenotype. It is known that conventional 2D culture of cells is often associated with a loss of phenotype and cell damage while 3D culture has been shown to retain cell phenotype. See Mayne, R. et al (1976) *PNAS*, 73, 5; Brodkin, K. R. et al (2004) *Biomaterials*, 25, 28; Elowsson, L. (2009) PhD Thesis (University of Sheffield, UK); Benya, P. D. and Schaffer, J. D. (1982) *Cell*, 30, 1; Bonaventure, J. et al (1994) *Experimental Cell Research*, 212, 1; and Osiecka, I. et at (2008) *Molecular Medicine Reports*, 1, 6. However, current technology does not allow for the exploitation of 3D culture advantages requires innovation to address the practical difficulties of 3D culture when compared to its simpler, 2D cell culture, predecessor.

One such exemplary technology lag area has been the process of cell passaging, in which a relatively small number of cells are repeatedly doubled for the sole purpose of creating a large number of cells (e.g., to achieve the number of cells necessary for a particular experiment). As one skilled in the art will appreciate, passaging cells in 2D is convenient and ubiquitously standardized. Additionally, during conventional passaging cells in 2D procedures, most cells enter into a state of rapid proliferation which decreases the time necessary to achieve the desired large number of cells. As one skilled in the art will appreciate, in conventional 2D passaging, cells respond to the stiffness of the material on which they attach. See, Attachment A, *Micro- and Nanoengineering of the Cell Microenvironment, Technologies and Applications (Engineering in Medicine & Biology)*, All Khademhosseini (Editor)).

Relative to tissues found in the body formed from organic materials, tissue culture lab ware is typically formed from stiff materials. For example and without limitation, the moduli of soft mammalian tissues ranges from about 100 Pa to about 950 kPa. Exemplary moduli of soft mammalian tissues include:

TABLE 1

A summary of elastic moduli of several different tissues. Experimental elastic moduli of a variety of tissues. including the animal of origin of the tissue, and the testing modality used to determine the modulus. When multiple stiffness values were available. the value at the lowest strain rate and lowest pre-strain was used to approximate the "resting stiffness" of the tissue

| Tissue type | Animal | Testing method | Elastic modulus | Ref |
| --- | --- | --- | --- | --- |
| Achilles' tendon | Rat | Tension | 310 Mpa | 15 |
| Articular cartilage | Bovine | Compression | 950 kPa | 86 |
| Skeletal muscle | Rat | Tension | 100 kPa | 87 |
| Carotid artery | Mouse | Perfusion | 90 kPa | 88 |
| Spinal cord | Human | Tension | 89 kPa | 89 |
| Thyroid cancer[a] | Human | Compression | 45 kPa | 16 |
| Spinal cord | Rat | Tension | 27 kPa | 90 |
| Cardiac muscle | Mouse | Tension | 20-150 kPa | 91 |
| Skeletal muscle | Mouse | AFM | 12 kPa | 13 |
| Thyroid | Human | Compression | 9 kPa | 16 |
| Lung | Guinea pig | Tension | 5-6 kPa | 5 |
| Breast tumor | Human | Compression | 4 kPa | 7 |
| Kidney | Swine | Rheology | 2.5 kPa | 92 |
| Premalignant breast[b] | Human | Indentation | 2.2 kPa | 14 |
| Fibrotic liver | Human | Compression | 1.6 kPa | 93 |
| Liver | Human | Compression | 640 Pa | 93 |
| Lymph containing metastases | Human | Vibrational resonance | 330 Pa | 17 |
| Brain | Swine | Indentation | 260-490 Pa | 94 |
| Lymph Nnode | Human | Vibrational resonance | 120 Pa | 17 |
| Mammary gland | Human | Compression | 160 Pa | 7 |
| Fat | Human | Indentation | 17 Pa | 14 |

[a]Thyroid papillary adenocarcinoma.
[b]Mammary ductal carcinoma in situ.
2 | *Soft Matter*, 2006, 2, 1-9
This journal is © The Royal Society of Chemistry 2006

See, *Soft Matter*, 2007, 3, 299-306, DOI: 10.1039/b610522j"Soft biological materials and their impact on cell function" Ilya Levental, Penelope C. Georges and Paul A. Janmey.

Exemplary tissue culture lab ware formed from polystyrene has an elastic modulus of 3-3.5 GPa, which is higher than the modulus of tissues formed from organic materials but not as high as the elastic modulus of bone (9 GPa). In this aspect, bone is a composite made up of inorganic minerals with high bulk moduli and organic materials which are much softer, and the contribution of the inorganic materials increases the modulus correspondingly. See, *Journal of Biomedical Materials Research* Part A Volume 67A, Issue 3, Pages 886-899 Published Online: 20 Oct. 2003, (bulk hydroxyl apatite modulus of 34-117 GPa).

Currently there are no commercially available products designed for 3D cell passaging. Published research on this topic to date has explored aspects of the potential use of 3D hydrogels (of hyaluronic acid and poly(NIPAM) respectively) for 3D cell passaging and has shown benefits of phenotype retention. See, TERMIS-EU 2010 Oral Presentation "Thermally-responsive Polymers for 3D Chondrocyte Culture;" and U.S. patent application Ser. No. 11/473,870 to Singh, which is incorporated herein by reference in its entirety. However, hydrogel matrices are not in the stiffness range of tissue culture polystyrene or bone.

What is needed in the art is a method for culturing cells in a dynamic environment in which the physical and biochemical conditions can be advantageously changed over the course of time. Moreover, what is needed is a system in which cells can be developed to form a three-dimensional construct, while maintaining the isolation and purity of the developing product cells. In another aspect, what is needed is a material and method for 3D cell passaging that the use of a stiff culture material in a 3D cell culture environment while maintaining a desired level of phenotype retention.

SUMMARY

In one aspect, the present invention is directed to a bioreactor system. The disclosed bioreactor system can comprise a single or a multiple culture system. In one aspect, a bioreactor system of the invention can comprise at least one culture chamber defining an inlet, an outlet, and a port that are in communication with an interior volume of the at least one culture chamber. In one non-limiting example, the at least one culture chamber comprises a first culture chamber and a second culture chamber. In this aspect, the first culture chamber defines a first inlet and a first outlet that is configured to allow fluid to selectively flow through the interior of the first culture chamber. In a further aspect, the first culture chamber defines a first port that is in communication with the interior of the first culture chamber. The second culture chamber defines a second inlet and a second outlet that is configured to allow a second fluid to selectively flow through the interior of the second culture chamber. In a further aspect, the second culture chamber defines a second port that is in communication with the interior of the second culture chamber.

In another aspect, the system can also comprise a membrane, which can be positioned, for example and without limitation, between the respective ports of adjoining first and second culture chambers. The membrane can be semipermeable and can have a porosity that is configured to allow passage of cellular expression products through the membrane, but prevent passage of the cells, which are disposed therein either chamber, through the membrane. In one embodiment, the membrane can be formed of a material, for example and without limitation a polycarbonate, which can discourage cellular attachment to the membrane.

In a further aspect, the bioreactor systems of the invention can comprise a cellular anchorage in one or both of the respective culture chambers. Suitable cellular anchorage can be formed of multiple discrete scaffolds or single continuous scaffolds. Multiple discrete scaffolds can be maintained within a culture chamber through utilization of a retaining mesh that can hold the scaffolding materials within the chamber and prevent the loss of the scaffolding materials through the outlet of the culture chamber.

In one aspect, a cellular anchorage can be maintained at a predetermined distance from the membrane that separates the chambers. In one aspect, this predetermined distance can be selected to effect prevention or minimization of attachment of cells to the membrane and can act to maintain the physical isolation of different cell types within their respective culture chambers.

The bioreactor system can also be capable of incorporating additional culture chambers that can be in biochemical communication with one or both of the other two culture chambers. For instance, the at least one chamber can further comprise a third chamber that can be configured to selectively house cells that can be selectively positioned in biochemical communication with the one or more of the system culture chambers, optionally with a membrane separating the first and third chambers, though this aspect is not a requirement of the system.

It is contemplated that, in operation, the bioreactors and the cells disposed therein can optionally be subjected to at least one mechanical stimuli. For example and without limitation, pressurized fluid perfusion through a culture chamber can subject developing cells to shear stress; an adjacent pressure module can be utilized to subject the interior of a culture chamber to hydrostatic loading, and the like.

It is also contemplated that the bioreactors of the system can be used for growth and development of isolated cells in various different applications. For instance, three-dimensional cellular constructs can be formed including only the cells that are isolated in one of the culture chambers of the reactor system. In one exemplary aspect, a culture chamber can be seeded with undifferentiated cells, and the method can comprise triggering differentiation of the cells via the biochemical triggers provided from the cells of the second culture chamber.

In a further aspect, it is contemplated that for tissue passaging, a material composition comprising two or more materials can be used. In one example, the material composition can comprise a stiff culture material having substantially large porosity into which a soft material has been introduced. In one example, and without limitation, the stiff culture material can be formed from metal, synthetic polymer, ceramic and the like. In one example, and without limitation, the soft material can be formed from a hydrogel or uncrosslinked oligomers of polymers either synthetic or of natural origin, and the like. In one aspect, the soft material can be configured or otherwise have a means for releasing the soft material from the stiff material. In one exemplary aspect, the releasing means can comprise chemical degradation or other change initiated by light, temperature, pH, chemical catalyst, and the like.

In yet another aspect, a method of 3D cell passaging is provided that comprises providing a population of cells to be passaged and introducing the population of cells into the material composition to which they attach to at least portions of the soft material. At a desirable and or predetermined time after the cells attachment, the method can further comprise causing the soft material to disassociate from the stiff material, thereby releasing the soft material and the cells from the stiff material of the material composition. In another aspect, the method can further comprise dividing the recovered cells, with or without remnants of the soft material, into multiple populations and repeating the method using the subdivided populations. It is of course contemplated that this process can be done recursively.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 3 is one embodiment of a bioreactor system of the present invention including two adjacent cell modules having independently controlled flow characteristics there through;

DETAILED DESCRIPTION OF THE INVENTION

Figure 1A:
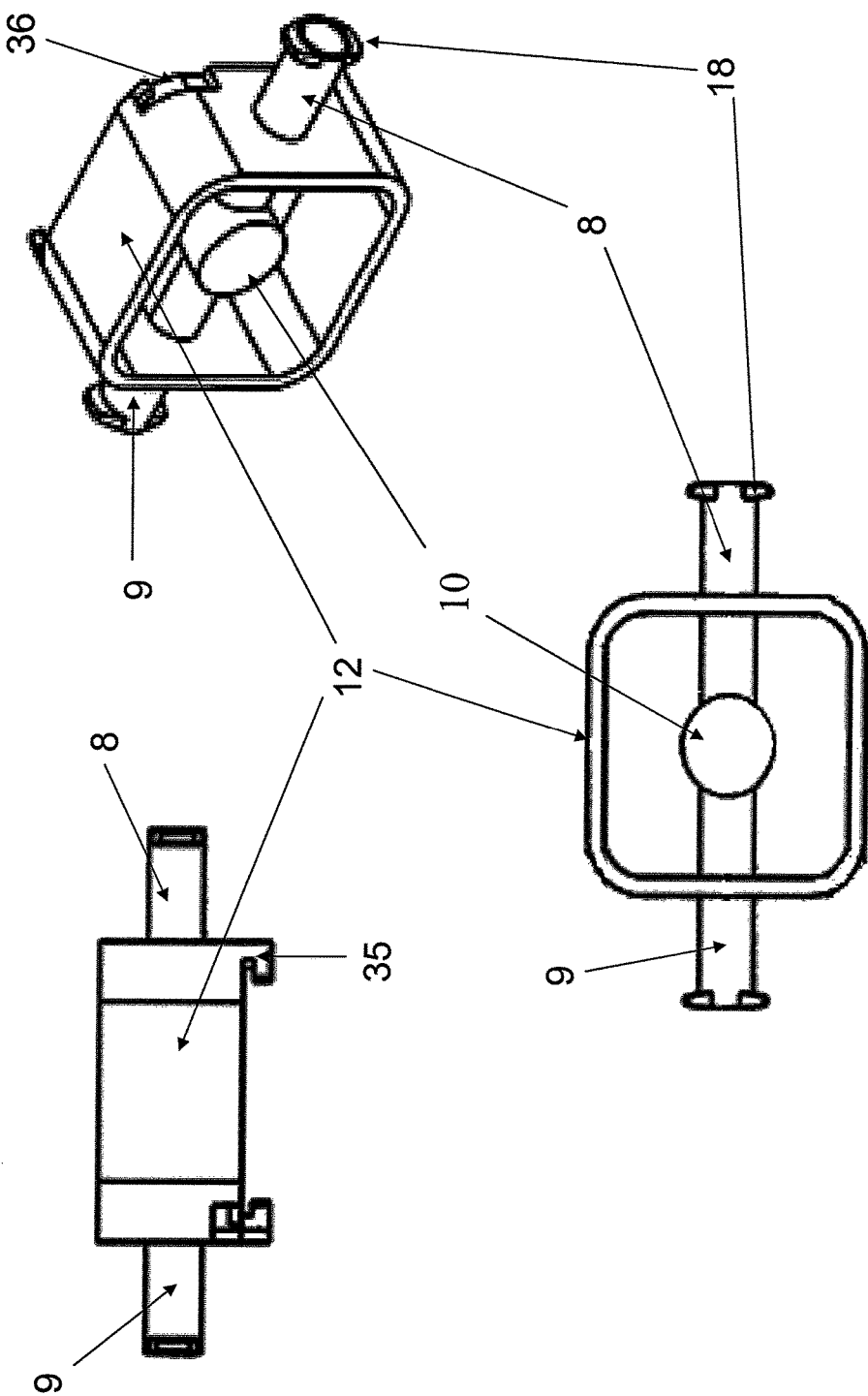
FIGS. 1A and 1B are views of one embodiment of the cell modules of the bioreactor system.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an," and "the" comprise plural referents unless the context clearly dictates otherwise. Thus, for example, reference to a "chamber" comprises aspects having two or more such chamber unless the context clearly indicates otherwise.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description comprises instances where said event or circumstance occurs and instances where it does not.

In simplest terms, disclosed herein are bioreactor systems. In one aspect, the bioreactor systems disclosed herein comprise at least one cell module defining a culture chamber, an inlet, an outlet, and at least one port opening. The cell modules of the bioreactor system can be engaged to form multi-chambered bioreactor systems. Thus, in one aspect, disclosed herein are bioreactor systems comprising at least one first cell module defining a first cell culture chamber, an inlet, an outlet, and a port opening, wherein the port opening is on one end of the cell culture chamber and at least one second cell module defining a second cell culture chamber, an inlet, an outlet, and a port opening, wherein the port opening is on one end of the cell culture chamber. It is understood that the first and second culture chambers respectively defining the first and second cell modules can be separated by a barrier such as a membrane. Thus, in another aspect, disclosed herein are bioreactor systems comprising at least one first cell module defining a first cell culture chamber, an inlet, an outlet, and a port opening, wherein the port opening is on one end of the cell culture chamber and at least one second cell module defining a second cell culture chamber, an inlet, an outlet, and a port opening, wherein the port opening is on one end of the cell culture chamber; a membrane positioned between the open port of said first cell module and the open port of said second cell module.

It is further understood that the first and second cell module can be physically engaged. Thus, in still another aspect, disclosed herein are bioreactor systems comprising at least one first cell module defining a first cell culture chamber, an inlet, an outlet, and a port opening, wherein the port opening is on one end of the cell culture chamber and at least one second cell module defining a second cell culture chamber, an inlet, an outlet, and a port opening, wherein the port opening is on one end of the cell culture chamber; a membrane positioned between the open port of said first cell module and the open port of said second cell module; and wherein the first cell module and second cell module are sealingly engaged securing the membrane between the first and second module.

The disclosed bioreactor systems can be assembled to allow for single or multiple cultures of tissues or cells. Thus, in one aspect, the bioreactor system is directed to multi-chambered systems, such as a co-culture bioreactor system, and can, for example, be utilized for the growth and development of isolated cells of one or more cell types in a dynamic in vitro environment more closely resembling that found in vivo. For instance, the multi-chambered bioreactor system can allow biochemical communication between cells of different types while maintaining the different cell types in a physically separated state, and moreover, can do so while allowing the cell types held in any one chamber to grow and develop with a three-dimensional aspect. In addition, the presently disclosed bioreactor system can allow for variation and independent control of environmental factors within the individual chambers. For instance, it is contemplated that the chemical make-up of a nutrient medium that can flow through a chamber as well as the mechanical force environment within the chamber including the perfusion flow, hydrostatic pressure, and the like, can be independently controlled and maintained for each separate culture chamber of the disclosed systems In yet another embodiment, undifferentiated stem cells can be located in a first chamber of the bioreactor system, and one or more types of feeder cells can be located in adjacent chamber(s), which, as one skilled in the art will appreciate, can selective be in biological communication with the first chamber. Such a bioreactor system can be utilized to, for example and without limitation, retain the differentiation state of cells in the first chamber and/or direct the course of their differentiation, as desired.

Cells and tissues used in the disclosed bioreactor systems and methods can be obtained by any method known to those of skill in the art. Examples of sources of cells and tissues include without limitation purchase from a reliable vendor, blood (including peripheral blood and peripheral blood mononuclear cells), tissue biopsy samples (e.g., spleen, liver, bone marrow, thymus, lung, kidney, brain, salivary glands, skin, lymph nodes, and intestinal tract), and specimens acquired by pulmonary lavage (e.g., bronchoalveolar lavage (BAL)). The source of cells and tissues obtained from blood, biopsy, or other direct ex vivo means can be any subject having tissue or cells with the desired characteristics including subject with abnormal cells or tissues which are characteristic of a disease or condition such as, for example, a cancer patient. Thus, it is contemplated herein that the subject can be a patient. It is also understood that there may be times where one of skill in the art desires normal tissues or cells. Thus, also disclosed herein are tissues and cells obtained form a normal subject wherein a "normal" subject refers to any subject not suffering from a disease or condition that affects the tissues or cells being obtained. It is further understood that the subject can comprise an organism such as a mouse, rat, pig, guinea pig, cat, dog, cow, horse, monkey, chimpanzee or other nonhuman primate, and human.

Therefore, it is contemplated that exemplary cell types comprise, at least partially and without limitation, cells having the following exemplary morphologies: Acinar cells, Adipocytes, Alveolar cells, Ameloblasts, Annulus Fibrosus Cells, Arachnoidal cells, Astrocytes, Blastoderms, Calvarial Cells, Cancerous cells (Adenocarcinomas, Fibrosarcomas, Glioblastomas, Hepatomas, Melanomas, Myeloid Leukemias, Neuroblastomas, Osteosarcomas, Sarcomas) Cardiomyocytes, Chondrocytes, Chordoma Cells, Chromaffin Cells, Cumulus Cells, Endothelial cells, Endothelial-like cells, Ensheathing cells, Epithelial cells, Fibroblasts, Fibroblast-like cells, Germ cells, Hepatocytes, Hybridomas, Insulin producing cells, Intersticial Cells, Islets, Keratinocytes, Lymphocytic cells; Macrophages, Mast cells, Melanocytes, Meniscus Cells, Mesangial cells, Mesenchymal Precursor Cells, Monocytes, Mononuclear Cells, Myeloblasts, Myoblasts, Myofibroblasts, Neuronal cells, Nucleus cells, Odontoblasts, Oocytes, Osteoblasts, Osteoblast-like cells, Osteoclasts, Osteoclast precursor cells, Oval Cells, Papilla cells, Parenchymal cells, Pericytess, Peridontal Ligament Cells, Periosteal cells, Platelets, Pneumocytes, Preadipocytes, Proepicardium cells, Renal cells, Salisphere cells, Schwann cells, Secretory cells, Smooth Muscle cells, Sperm cells, Stellate Cells, Stem Cells, Stem Cell-like cells, Stertoli Cells, Stromal cells, Synovial cells, Synoviocytes, T Cells, Tenocytes, T-lymphoblasts, Trophoblasts, Urothelial cells, Vitreous cells, and the like; said cells originating from, for example and without limitation, any of the following tissues: Adipose Tissue, Adrenal gland, Amniotic fluid, Amniotic sac, Aorta, Artery (Carotid, Coronary, Pulmonary), Bile Duct, Bladder, Blood, Bone, Bone Marrow, Brain (including Cerebral Cortex), Breast, Bronchi, Cartilage, Cervix, Chorionic Villi, Colon, Conjunctiva, Connective Tissue, Cornea, Dental Pulp, Duodenum, Dura Mater, Ear, Endometriotic cyst, Endometrium, Esophagus, Eye, Foreskin, Gallbladder, Ganglia, Gingiva, Head/Neck, Heart, Heart Valve, Hippocampus, Iliac, Intervertebral Disc, Joint, Jugular vein, Kidney, Knee, Lacrimal Gland, Ligament, Liver, Lung, Lymph node, Mammary gland, Mandible, Meninges, Mesoderm, Microvasculature, Mucosa, Muscle-derived (MD), Myeloid Leukemia, Myeloma, Nasal, Nasopharyngeal, Nerve, Nucleus Pulposus, Oral Mucosa, Ovary, Pancreas, Parotid Gland, Penis, Placenta, Prostate, Renal, Respiratory Tract, Retina, Salivary Gland, Saphenous Vein, Sciatic Nerve, Skeletal Muscle, Skin, Small Intestine, Sphincter, Spine, Spleen, Stomach, Synovium, Teeth, Tendon, Testes, Thyroid, Tonsil, Trachea, Umbilical Artery, Umbilical Cord, Umbilical Cord Blood, Umbilical Cord Vein, Umbilical Cord (Wartons Jelly), Urinary tract, Uterus, Vasculature, Ventricle, Vocal folds and cells, and the like; said tissues which originate, for example and without limitation, in any of the following species: Baboon, Buffalo, Cat, Chicken, Cow, Dog, Goat, Guinea Pig, Hamster, Horse, Human, Monkey, Mouse, Pig, Quail, Rabbit, and the like.

Figure 1B:
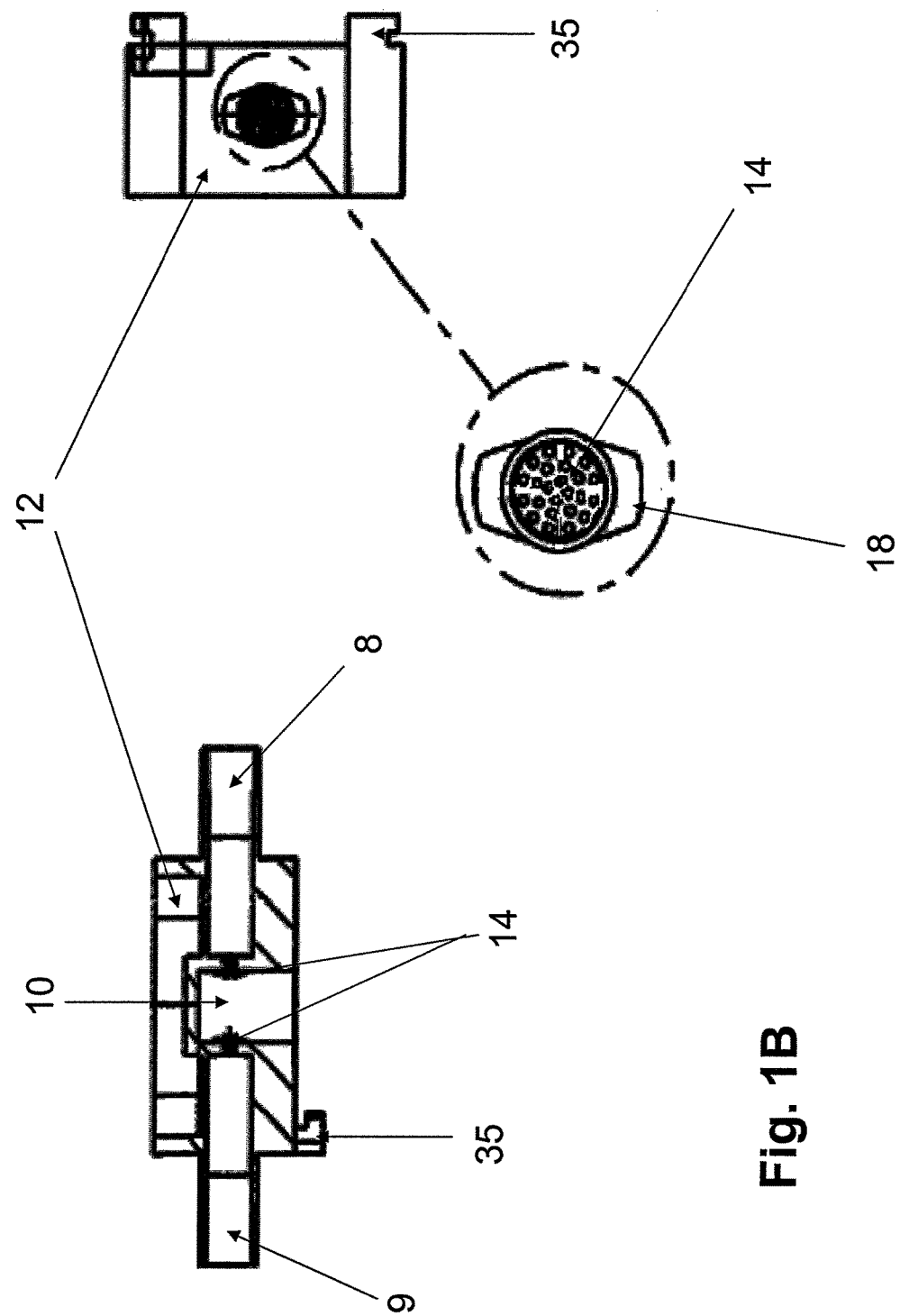

Referring to FIGS. 1A and 1B, a view of one embodiment of the bioreactor system is illustrated. In one aspect, the bioreactor system 2 comprises at least one individual culture chamber 10, which is defined therein a cell module 12. The dimensions and overall size of a cell module 12, and culture chamber 10, are not critical to the invention. In general, a cell module 12 can be of a size so as to be handled and manipulated as desired, and so as to provide access to the culture chambers either through disassembly of the device, through a suitably located access port, or according to any other suitable method. As one skilled in the art will appreciate, the culture chamber 10 defined by the module 12 can generally be of any size as long as adequate for the assigned task. In one aspect, nutrient flow can be maintained throughout a three-dimensional cellular construct growing in the culture chamber 10, so as to prevent cell death at the construct center due to lack of nutrient supply.

Thus, in one aspect, one embodiment is a cell module 12. Though each cell module 12 of the embodiment illustrated in FIG. 1 can comprise a single culture chamber 10, or, optionally, a single cell module 12 can comprise multiple culture chambers. In the latter aspect, each culture chamber of the module can comprise individual access ports (described further below), so as to provide individualized flow through each culture chamber and independent control of the local environmental conditions in each culture chamber. While the materials from which the module 12 can be formed can generally be any moldable or otherwise formable material, the surface of the culture chamber 10, as well as any other surfaces of the module that may come into contact with the cells, nutrients, growth factors, or any other fluids or biochemicals that may contact the cells, should be of a suitable sterilizable, biocompatible material. In one particular embodiment, components of the system can also be formed so as to discourage cell anchorage at the surfaces.

It is also contemplated herein that the cell module 12 and the components that make up the cell module 12 can be constructed from a single mold rather than attaching individual pieces. That is, disclosed herein are bioreactor systems wherein each cell module comprises a monolithic construction. The advantage of such construction provides increased sterility and removes possibilities of leaks forming. Thus, in one aspect, the cell module 12 can be constructed of any material suitable to being formed in a mold.

In one embodiment two cell modules 12 can be selectively coupled via a compression fitting so form two culture chambers 10 that are adjoined and are in selective biological communication with each other. Thus, in one aspect, the cell modules 12 can comprise a means for sealingly engaging the top surface of one module with the top surface of another module. It is understood that once fully engaged, the two cell modules can selectively, and optionally releasably, lock into place. In one aspect, it is contemplated that the means for sealingly engaging the respective cell modules will cause a compressive force to be effected on the adjoined surfaces of the respective modules. It is understood that there are many means for sealingly engaging two cell modules 12. One such method is shown in FIG. 1A. In this aspect, a male compression fitting 35 can be configured to sealingly engage the fitting 36 to form a compression fitting. In one aspect, the fitting 36 can have a raised portion and the male compression fitting 35 an indentation that when aligned form a lock. It is understood that such an engagement means could be engaged using a press and twisting motion. It is further understood that said engagement means could be disengaged by twisting in the opposite direction. It is further understood that the cell module 12 comprises both the male compression fitting 35 and female fittings 36 on the same or opposing faces of the cell module 12. For example, the cell module 12 can comprise male compression fittings on one face and female fittings 36 on the opposite face. Alternatively, the cell module 12 can comprise male compression fittings 35 and female fittings 36 on the same face. It is understood that the placement of the male fittings 35 and female fittings 36 is such that compression and stability are maximized, for example, with male compression fittings 35 being at opposite corners or sides from each other but adjacent to female fittings 36 which are on opposite sides or corners from each other.

Alternatively, the two cell module system can comprise a first cell module 12 and a second cell module 12, wherein the first and second module comprise identical cell chambers 10, inlets, and outlets, but wherein the first cell module 12 comprises one or more male compression fittings and the second cell module 12 comprises one or more female fittings. For example, the first cell module 12 can comprise only male compression fittings 35 and the second cell module 12 can comprise only female fittings 36. In an alternative example, the top surface of the first cell module 12 can comprise a raised perimeter with a convex bevel located at the mid point to three fourths point on the interior wall of the raised perimeter. The top surface of the second cell module 12 can have a perimeter relief that is of a depth to receive the male fitting on the first cell module. Additionally, the relief on the second cell module 12 can have a concave indentation which can form a lock when the convex bevel of the first cell module 12 is engaged. Similarly, the first and second cell modules 12 can be threaded in such a manner to allow the first module to be screwed down on the second module.

Thus, in one aspect a cell culture system can comprise first and second cell modules 12 capable of engaging wherein the first and second cell module are identical and interchangeable. In another aspect, the cell culture system can comprise a first and second cell module 12, wherein the first and second cell module are not identical or interchangeable but capable of being engaged.

It is further contemplated that the cell culture systems disclosed herein can comprise one or more first and second cell modules. The cell culture systems can have cell modules 12 independently controlled or serially linked through the outlet of one first and second cell module to the inlet of a second first and second cell module. The connections of inlets and outlets to media source, reagents, or flow source can be regulated by valves or linked directly to said source. Alternatively when serial linking is used, the outlet of one cell module 12 can be directly linked to the inlet of a second cell module 12 or have a controlled connection such as with a valve.

The culture chamber 10 can generally be of a shape and size so as to cultivate living cells within the chamber. In one preferred embodiment, culture chamber 10 can be designed to accommodate a biomaterial scaffold within the culture chamber 10, while ensuring adequate nutrient flow throughout a cellular construct held in the culture chamber 10. For instance, a culture chamber 10 can be between about 3 mm and about 10 mm in any cross sectional direction. In another embodiment, the culture chamber can be greater than about 5 mm in any cross sectional direction. For instance, the chamber can be cylindrical in shape and about 6.5 mm in both cross sectional diameter and height. The shape of culture chamber 10 is not critical to the invention, as long as flow can be maintained throughout a cellular construct held in the chamber.

It is understood that the formation of the culture chamber creates a volumetric reservoir or a size determined by the cross sectional direction and depth of the chamber. Accordingly, it is understood that the disclosed culture chambers 10 can be between 1 μL and 50 mL, 50 μL and 1 mL, 100 μL, and 500 μL, or 250 μL or any volume therebetween. Typically the culture chamber is circular or oval in cross sectional shape. However, it is further understood that the cross sectional shape of the culture chamber 10 can also be hexagonal, heptagonal, octagonal, nonagonal, decagonal, hendecagonal, dodecagonal, or larger polygon in shape. Additionally, it is contemplated herein that the closed end of a cell culture chamber 10 can be flat or convex. It is understood that fewer angles and abrupt changes in plane encourages cells to avoid adhering to the walls of the culture chamber and reduce turbulence of fluids passing through the chamber. Thus, it is contemplated herein that the shape of the culture chamber can be selected based on the particular characteristics one of skill in the art desires to replicate.

In one aspect, the culture chamber 10 is defined by an open end port on the top surface of the cell module 12 and a closed end on the bottom surface of cell module 12. The open end allows for the addition for cell anchorage and cells and can be sealed by a membrane 23 (see FIG. 2). It is also contemplated that the culture chamber can be open at both ends and, in this aspect, the open ends of the culture chamber 10 are defined in the respective top and bottom surfaces of the cell module 12. In another aspect the culture chamber 10 is defined by an opened end port on both the top and bottom surface. As one skilled in the art will appreciate, when the culture chamber 10 is defined by two opened ports, the open ended ports can be closed by mating the cell module 12 with a second cell module 12 and placing a membrane between the respective cell culture chambers 10. Thus, in another aspect, disclosed herein are bioreactor systems further comprising at least one third cell module, wherein the third cell module comprises a cell chamber open at both ends, wherein the cell chamber of the third cell module is closed by sealingly engaging the first and second cell modules on opposite faces of the third cell module 12.

In another aspect, the system can comprise a material composition. For example, it is contemplated that the material composition can be configured to serve as a cell anchorage that can be contained in the culture chamber 10. The term "cell anchorage" as utilized herein refers to one or more articles upon which cells can attach and develop. For instance, the term "cell anchorage" can refer to a single continuous scaffold, multiple discrete scaffolds, or a combination thereof. The terms "cell anchorage," "cellular anchorage," and "anchorage" are intended to be synonymous. It is contemplated that any suitable cell anchorage as is generally known in the art can be located in the culture chamber 10 to provide anchorage sites for cells and to encourage the development of a three-dimensional cellular construct within the culture chamber 10.

For purposes of the present disclosure, the term continuous scaffold is herein defined to refer to a construct suitable for use as a cellular anchorage that can be utilized alone as a single, three-dimensional entity. A continuous scaffold is usually porous in nature and has a semi-fixed shape. Continuous scaffolds are well known in the art and can be formed of many materials, e.g., coral, collagen, calcium phosphates, synthetic polymers, and the like, and are usually pre-formed to a specific shape designed for the location in which they will be placed. Continuous scaffolds are usually seeded with the desired cells through absorption and cellular migration, often coupled with application of pressure through simple stirring, pulsatile perfusion methods or application of centrifugal force.

Discrete scaffolds are smaller entities, such as beads, rods, tubes, fragments, or the like, for example tubes for the formation of vascular tubes. When utilized as a cellular anchorage, a plurality of identical or a mixture of different discrete scaffolds can be loaded with cells and/or other agents and located within a void where the plurality of entities can function as a single cellular anchorage device. Exemplary discrete scaffolds suitable for use in the present invention that have been found particularly suitable for use in vivo are described in U.S. Pat. No. 6,991,652, which is incorporated herein in it's entirety by reference. A cellular anchorage formed of a plurality of discrete scaffolds can be preferred in certain embodiments of the bioreactor system as discrete scaffolds can facilitate uniform cell distribution throughout the anchorage and can also allow good flow characteristics throughout the anchorage as well as encouraging the development of a three-dimensional cellular construct.

In one embodiment, for instance when considering a cellular anchorage including multiple discrete scaffolds, the anchorage can be seeded with cells following assembly and sterilization of the system. For example, an anchorage including multiple discrete scaffolds can be seeded in one operation or several sequential operations. Optionally, the anchorage can be pre-seeded, prior to assembly of the system. In one aspect, the anchorage can comprise a combination of both pre-seeded discrete scaffolds and discrete scaffolds that have not been seeded with cells prior to assembly of the bioreactor system.

The good flow characteristics possible throughout a plurality of discrete scaffolds can also provide for good transport of nutrients to and waste from the developing cells, and thus can encourage not only healthy growth and development of the individual cells throughout the anchorage, but can also encourage development of a unified three-dimensional cellular construct within the culture chamber. Thus, it is understood the scaffolds and matrices utilized herein can comprise shapes akin to real tissues with meaningful volumes.

The materials that are used in forming an anchorage can generally be any suitable biocompatible material. In one embodiment, the materials forming a cellular anchorage can be biodegradable. For instance, a cellular anchorage can comprise biodegradable synthetic polymeric scaffold materials such as, for example and without limitation, polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, and the like, and copolymers of the same. Optionally, an anchorage can comprise naturally derived biodegradable materials including, but not limited to, chitosan, agarose, alginate, collagen, hyaluronic acid, and carrageenan (a carboxylated seaweed polysaccharide), demineralized bone matrix, and the like, and copolymers of the same.

It is contemplated that exemplary scaffold materials can comprise, at least partially and without limitation: Collagen; PLA/poly(lactide); PLGA/poly(lactic-co-glycolic acid;) Chitosan; PCL/poly(e-caprolactone); Alginate/sodium alginate; PGA/poly(glycolide); Hydroxyapatite; Gelatin; Matrigel™; Fibrin; Acellular/Allogenic Tissue (all forms); Hyaluronic Acid; PEG/poly(ethylene glycol); Peptide; Silk Fibroin; Agarose/Agar; Calcium phosphate; PU/polyurethane; TCP/tri calcium phosphate; Fibronectin; PET/poly (ethylene terephthalate); Bioglass; PVA/Polyvinyl alcohol; Laminin; GAG/glycosaminoglycan; Cellulose; Titanium; DBP/demineralized bone powder; Silicone; PEGDA/PEG-diacrylate; Fibrinogen; Acellular/Allogenic Tissue-SIS; PDMS/polydimethylsiloxane; Acellular/Allogenic Tissue-Bone; ECM (in situ derived); Polyester; Elastin; PS/polystyrene; Glass; PBT/polybutylene terephthalate; Dextran; PEG/poly(ethylene glycol)-other modified forms; PES/polyethersulfone; PLL/poly-l-lysine; MWCNT/multiwalled carbon nanotube; PRBV/poly(hydroxybutyrate-co-hydroxyvalerate); Coral; Starch; PPF/poly(propylene fumarate); PLCL/poly(lactide-co-e-caprolactone); Chondroitin Sulfate; PAM/polyacrylamide; PC/polycarbonate; PEUU/poly(ester urethane)urea; Calcium carbonate; Atelocollagen; PHB/poly (hydroxybutyrate); Polyglactin; Gelfoam®; Acellular/Allogenic Tissue-Vasculature; PuraMatrix™; PAA/poly(acrylic acid); PA/polyamide (Nylon); Clot; PDO/polydioxanone; PMMA/poly(methyl methacrylate) (acrylic); Acellular/Allogenic Tissue-Heart Valve; PHEMA/poly(hydroxyethyl methacrylate); PVF/polyvinyl formal; PGS/poly(glycerol sebacate); PEO/poly(ethylene oxide); Acellular/Allogenic Tissue-Cartilage; Pluronic® F-127; PHBHHx/PHB-co-hydroxyhexanoate; PHP/polyHIPE polymer; Polyphosphazene; Silicate; Poly-D-lysine; Poly peptide/MAXI; Aluminum oxide; PTFE/polytetrafluoroethylene; Silica/silicon dioxide; SWCNT/single-walled carbon nanotube; Cytomatrix® (Tantalum); PLG/poly(L-lactide-glycolide); ORMOCER®; POSS/polyhedral oligomeric silsesquioxanes; Acellular/Allogenic Tissue-Tendon; HEWL/Hen egg white lysozyme; Polyelectrolyte; Polyamidoamine; POC/poly(octanediol citrate); PEI/polyethyleneimine; Hyaff-11®; PTMC/poly(trimethylene carbonate); PAAm/Poly(allylamine); Polyester utethane; Lactose; PNiPAAm/poly(N-isopropylacrylamide); Polyurethane-urea; Keratin; Cyclic Acetal; NiPAAm; Poly HEMA-co-AEMA; PE/polyethylene (all forms); PLDLA/poly(L/D)lactide; Vitronectin; PDL/poly-D-lysine; Corn starch; TMP/trimethylolpropane; Poloxamine; Acellular/Allogenic Tissue-Skin; Gellan gum; PEMA/poly(ethyl methacrylate); Tantalum; DegraPol®; Silastic;

Akermanite; Polyhydroxyalkanoate; AlloDerm®; Polyanhydrides; Zirconium Oxide; Polyether; TMC/trimethylene carbonate; Sucrose; PEVA/poly(ethylene-vinyl alcohol); PMAA/poly(methacrylic acid); Hydrazides; Poly(diol citrate); PVDF/polyvinylidene fluoride; COBB/Ceramic Bovine Bone; PVLA/polyvinylbenzyl-D-lactoamide; PCU/poly(carbonate-urea)urethane; MBV; Chitin; Synthetic elastin; PBSu-DCH/diisocyanatohexane-extended poly(butyl); PANI/polyaniline; Polyprenol; Zein; Egg Shell Protein; EVA/Ethylene Vinyl Acetate; Gliadin; HPMC/hydroxypropyl methylcellulose; PE/phthalate ester; Thrombin; PP/Polypropylene; OptiCell™; PEEP/poly(ethyl ethylene phosphate); OCP/Octacalcium Phosphate; PEA/poly(ester amide); Aggrecan; Graphite; NovoSorb™; PLO/poly-L-ornithine; DOPE/dioleoyl phosphatidylethanolamine; ELP/Elastin-like polypeptide; LDI/lysine diisocyanate; PPC/poly(propylene carbonate); Plasma; Fe(CO)(5)/Iron pentacarbonyl; Asbestos; PPE/polyphosphoester; Azoamide; Triacrylate; PRP/platelet-rich plasma; Dextran (modified forms); PGSA/poly(glycerol-co-sebacate)-acrylate; Polyorthoester; SPLE/sodium polyoxyethylene lauryl ether sulfate; Methacryloyloxy; TGA/thioglycolic acid; PCTC/poly(caprolactone-co-trimethylene carbonate; SU-8; SLG/sodium N-lauroyl-L-glutaminate; Polysulfone; Phosphophoryn; HEA/hydroxyethyl acrylate; PSSNa/poly(sodium styrene sulfonate); Carbon Foam; PFOB/perfluorooctyl bromide; Lecithin; Mebiol®; BHA/butylated hydorxyanisole; Surgisis®; OsSatura™; Skelite™; Cytodex™; COLLOSS®; E; Magnesium; PAN/polyacrylonitrile; HPMA/hydroxypropylmethacrylamide; Lutrol® F127; PDTEc/poly(desaminotyrosyl-tyrosineethyl esterc; Rayon (commercial product); Organo Clay; Portland Cement; Xyloglucan; Vaterite Composites (SPV); PRx/polyrotaxane; AW-AC/anti-washout apatite cement; Starch acetate; Nicotinamide; POR/poly-L-ornithine hydrobromide; AM-co-VPA/acrylamide-co-vinyl phosphonic acid; Calcium Silicate; Carbylan GSX; Colchicine; GPTMS/glycidoxypropyltrimethoxysilane; Phosphorylcholine; PLE/polyoxyethylene lauryl ether; Tartaric acid; HPA/hydroxyphenylpropionic acid; PLVA/poly-N-p-vinyl-benzyl-D-lactonamide; PEOT/polyethyle-neoxide-terephtalate; Adipose Tissue Powder; SLS/sodium lauryl sulfate; KLD-12 peptide; PDTOc/poly(desaminotyrosyl-tyrosine octylesterc; Si-TCP/silicate-substituted tricalcium phosphate; PCLF/polycaprolactone fumarate; PAMPS/poly(acrylamidomethylpropanesulfonicsodiu; Bio-Oss®; MGL/mono glyceryl laurate; DMA/fullerene C-60 dimalonic acid; THF/tetrahydrofuran; Polyphosphoester; Paper; Calcium-silicon; PPD/poly-p-dioxanone; BME/Basement Membrane Extract (generic); and OPF/oligo[poly(ethylene glycol)fumarate].

A biodegradable anchorage can comprise factors that can be released as the scaffold(s) degrade. For example, an anchorage can comprise within or on a scaffold one or more factors that can trigger cellular events. According to this aspect, as the scaffold(s) forming the cellular anchorage degrades, the factors can be released to interact with the cells. Referring again to FIGS. 1A and 1B, in those embodiments including a cellular anchorage formed with a plurality of discrete scaffolds, a retaining mesh 14 can also be located within the culture chamber 10. The retaining mesh 14 can be formed of any suitable biocompatible material, such as polypropylene, for example, and can line at least a portion of a culture chamber 10, so as to prevent material loss during media perfusion of the culture chamber 10. Alternatively, the retaining mesh can be a located at the opening of the inlet and outlet of the culture chamber 10. The retaining mesh 14 can be an integral part of the inlet and outlet so as to be made of the same material and in the same form as the cell module 12 such that the retaining mesh 14 is not removable for the cell module 12. A porous retaining mesh 14 can generally have a porosity of a size so as to prevent the loss of individual discrete scaffolds within the culture chamber 10. For example, a retaining mesh 14 can have an average pore size of between about 10 µm and about 1 mm, between about 50 µm and about 700 µm, or between about 150 µm and about 500 µm.

Upon assembly of the bioreactor system, two (or more) culture chambers 10 can be aligned so as to be immediately adjacent to one another. In one aspect, to help create a fluid-proof seal of the system, a gasket 16 and a permeable membrane portion 23 can be positioned between the adjoining surfaces of the cell modules to selectively prevent fluid leakage from between the respective open ends (the respective ports of the culture chambers). In one aspect, the gasket 16 and the membrane portion 23 can be formed as a single integrated structure. It is contemplated that the membrane portion 23 of gasket 16 can be positioned between the respective ports adjoined culture chambers 10 and can have a porosity that can allow biochemical materials, for instance growth factors produced by a cell in one chamber, to pass through the membrane and into the adjoining chamber, where interaction can occur between the biochemical material produced in the first chamber and the cells contained in the second chamber.

Optionally, the two or more culture chambers 10 can be aligned with only the membrane portion 23 positioned between the adjoining surfaces of the cell modules and in over/underlying relationship to the respective ports of the adjoining chambers. In operation, by interlocking two cell modules 12, the membrane portion 23 can be compressed therebetween the adjoining surface to effect a fluid-proof seal around the ports of the culture chamber 10. Thus, in this exemplary aspect, the membrane acts as a gasket. In a further alternative embodiment, at least one of the cell modules can comprise a raised convex concentric ring which encircles the open end, the port, of the culture chamber 10 on the top surface of the cell module 12. In this aspect, when the two cell modules are interlocked the added pressure placed on the raised area effects a seal on the membrane that is interposed therebetween. In a further aspect, the cell modules can comprise a male and female cell module where the male module comprises a raised convex concentric ring which encircles the open end, the port, of the culture chamber 10 on the top surface of the cell module 12 and the female cell module comprises a concave concentric ring which encircles the culture chamber 10 on the top surface of the female cell module 12. When the male and female cell modules are engaged, the male and female rings form a bight in the membrane creating a seal and aid in alignment of the culture chambers 12.

In bioreactor systems where a membrane is used without a gasket, the membrane becomes a gasket by compressing the membrane under the compression formed by the interlocking of two or more cell modules 12. Therefore, it is understood and herein contemplated that the membrane can comprise a compressible material that is conducive to the formation of a gasket. Such materials are well known to those of skill in the art.

In various aspects, it is contemplated that the membrane 23 can be a solid, non-porous, or semi-permeable (i.e., porous) membrane. The porosity can be small enough to prevent passage of the cells or cell extensions from one chamber to another. In particular, the membrane porosity can be predetermined so as to discourage physical contact between the cells held in adjacent chambers, and thus maintain isolation of the cell types. Suitable porosity for a membrane can be determined based upon specific characteristics of the system, for instance the nature of the cells to be cultured within the chamber(s). Such determination is well within the ability of one of ordinary skill in the art and thus is not discussed at length herein.

Additionally, the membrane 23 can comprise not only material that affects the transmission of physical parameters, but optical transmission as well. Thus, contemplated herein are membranes 23 wherein the membrane only allows the transmission of certain wavelengths of light to pass from one side of the membrane to the other or excludes specific wavelengths of light.

Alternatively, the membrane 23 can comprise a composite structure of both porous and non-porous or solid membranes, which allow the removal of one non-porous membrane while the other porous membrane remains in place between the culture chambers 10. In one aspect, the non-porous or solid membrane can be affixed to the porous membranes and separated from the porous membrane without needing to remove the semi-permeable membrane. Thus, the solid membrane allows for separate culturing conditions and media usage; whereas a porous membrane allows for the passage of biochemical materials. In another aspect, the membrane 23 comprising a porous and solid or nonporous membrane can be placed between adjoined culture chambers to allow for separate culture conditions and after a period of time the solid or non-porous membrane can be removed to allow for passage of biochemical materials.

In another alternative, the membrane 23 can comprise a biodegradable material. Through the use of a biodegradable material for the membrane 23, porosity can be electively increased over the course of the usage of the membrane. For example, a non-porous membrane 23 made of biodegradable material can be used which prevents the exchange of culture conditions. In operation, as the material is used, the membrane degrades allowing for the exchange of biochemical materials. In a further alternative, the membrane 23 can comprise biodegradable and non-biodegradable material such as a porous non-biodegradable membrane where the pores are sealed with a biodegradable material or coating. As the biodegradable material or coating is dissolved, the non-degradable porous membrane is revealed.

In another embodiment the cells contained in a culture chamber 10 can be maintained at a distance from the membrane 23 to discourage physical contact between cells held in adjacent culture chambers. For instance, in this example, retaining mesh 14 can be located between a cell anchorage held in a culture chamber and the membrane located between two adjacent chambers. The width of the retaining mesh 14 can prevent contact of the cells with the membrane 23. Optionally, the retaining mesh 14 can be at a distance from the membrane 23, providing additional separation between the membrane 23 and cells held in the culture chamber 10. In another embodiment, a continuous scaffold can be located in a culture chamber 10 at a distance from the membrane 23 so as to discourage physical contact between the cells held in the culture chamber and the membrane 23. While a preferred distance between the membrane 23 and cells held in the chamber will vary depending upon the specific characteristics of the system as well as the cells to be cultured in the system, in general, the distance between the two can be at least about 100 microns.

Each culture chamber 10 of the system can comprise the capability for independent flow control through the chamber. For example, and referring again to FIGS. 1A and 1B, each individual culture chamber 10 can comprise an inlet 8 and an outlet 9 through which medium can flow. In this exemplary aspect, the inlet 8 and outlet 9 can be connected to medium perfusion tubing via quick-disconnect luers 18 and stopcock valves, but this particular arrangement is not a requirement of the invention, and any suitable connection and perfusion system as is generally known in the art can be utilized. In another embodiment, the connection can be an integral portion of a single formed module 12. For example, the luers 18 can be formed at the outward ends of the inlet 8 and outlet 9 as shown in FIG. 1. It is understood and herein contemplated that other means for attaching tubing and stopcock valves are well known in the art and can be used in the present invention as an alternative to a luer lock. Such attachment mechanisms comprise but are not limited to compression fittings, threaded fittings, and friction.

It is contemplated that at least portions of the respective inlet 8 and outlet 9 can be straight or can comprise one or more bends. It is understood that the inlet 8 and outlet 9 do not have to line up within the culture chamber 10, but can be situated at opposing ends (i.e., one at the top and another the bottom as reflected in the middle module in FIG. 4). It is contemplated that the respective shapes of the inlet and outlet can be configured to affect the desired flow characteristics within the chamber.

Figure 2:
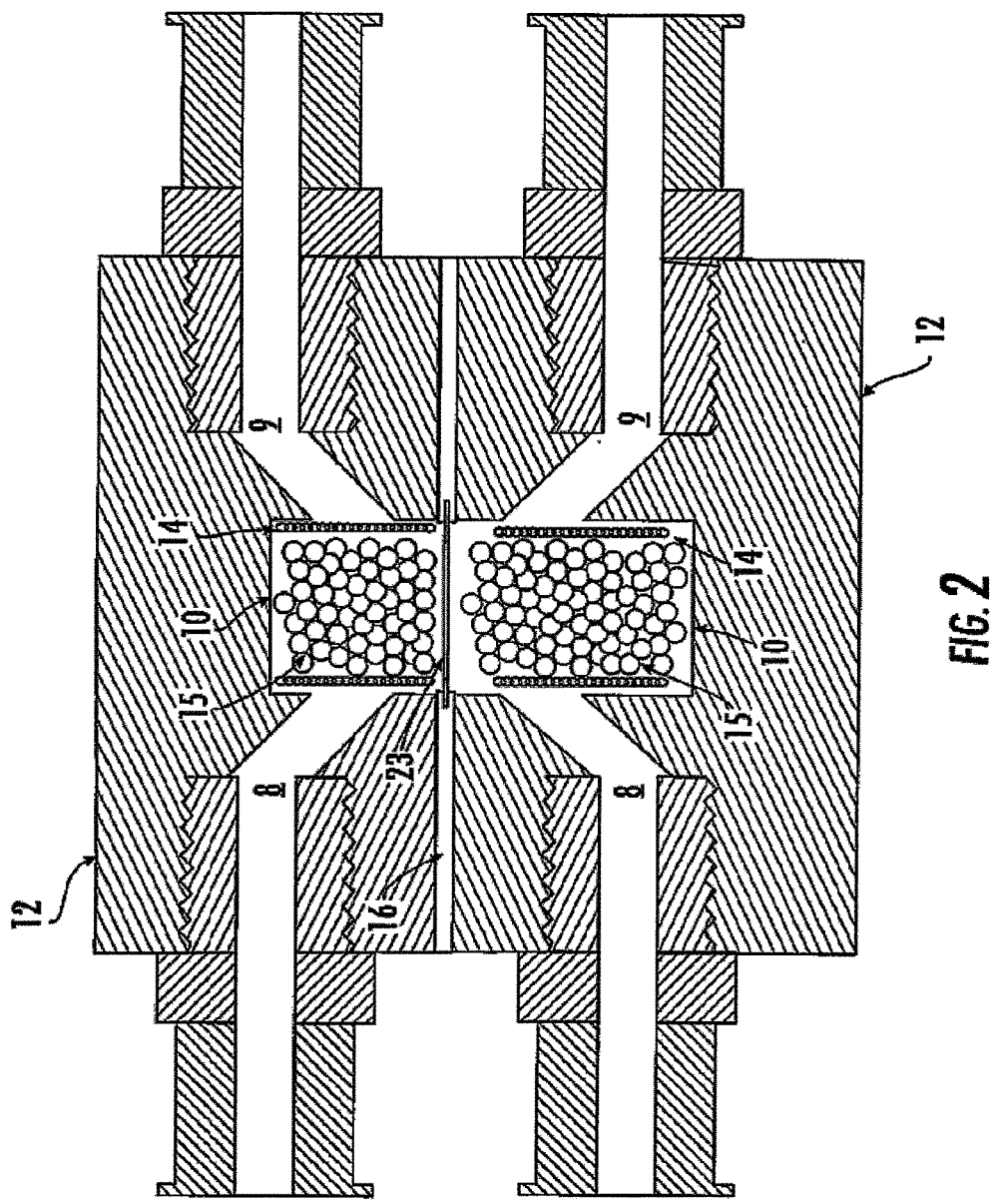
FIG. 2 is a schematic diagram of the embodiment of FIG. 1 following assembly such that the two cell modules are adjacent and allow biochemical communication between cells held in the two adjacent modules.

Referring to FIG. 2, one aspect of a pair of adjoined modules 12 following assembly is shown. As can be seen, the embodiment comprises two modules 12, each of which comprises a single culture chamber 10. Upon assembly, the two culture chambers 10 are aligned with the permeable membrane portion 23 of gasket 16 positioned therebetween the ports of the culture chambers. In this particular embodiment, a plurality of discrete scaffolds 15 has been located within each of the two culture chambers 10 as a cellular anchorage. In addition, each culture chamber 10 can be lined with a retaining mesh 14, as shown. Upon assembly, desired media can be independently perfused through each culture chamber 10 via the separate inlets 8 and outlets 9.

Figure 3:
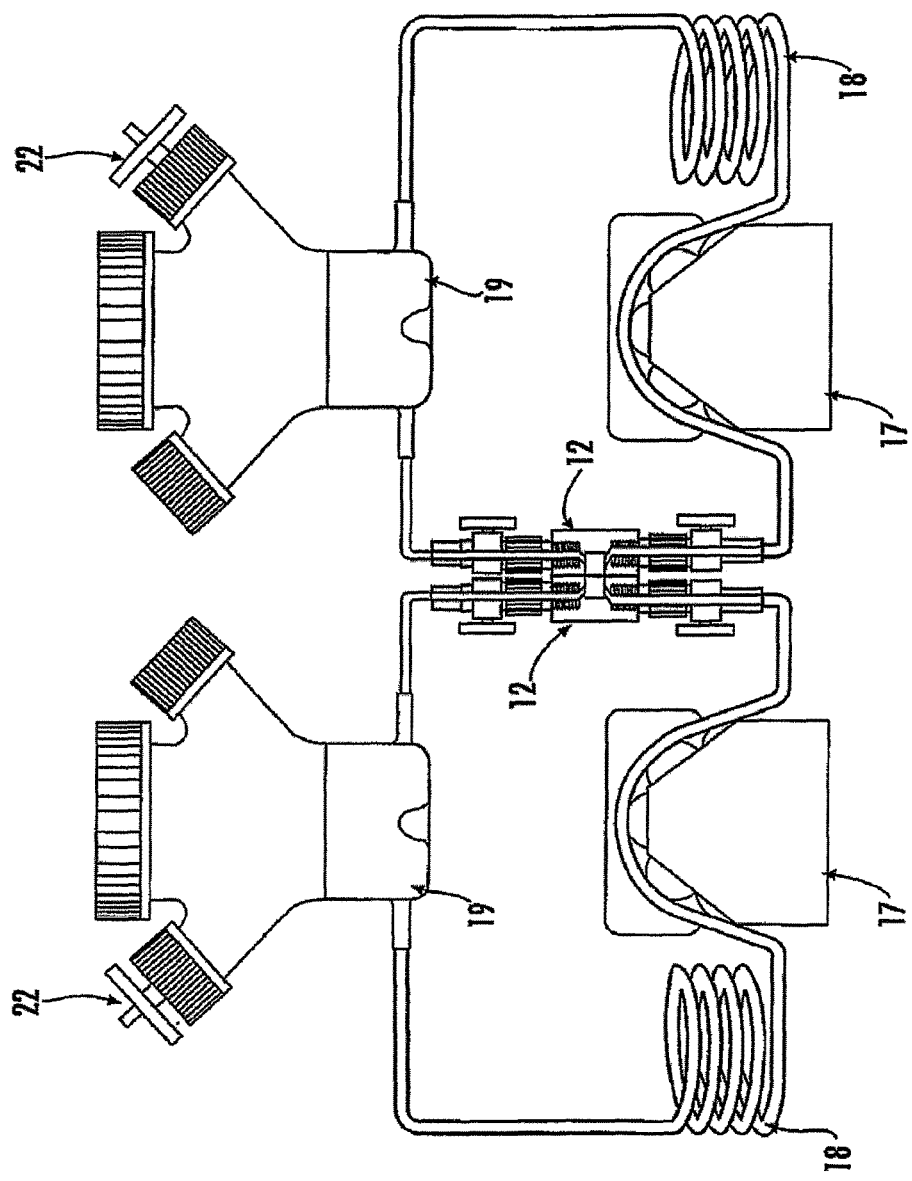

FIG. 3 illustrates one embodiment of a bioreactor system according to the present invention. This aspect comprises two assembled modules 12, such as those illustrated in FIG. 2, each in line in a flow circuit that is completely independent of the other that includes a pump 17, for instance a peristaltic pump and a media container 19. In this aspect, gas exchange can be facilitated by two methods, including a first method utilizing a coiled length of a gas permeable tubing 18 such as, for example, a platinum-cured silicone tubing, as well as a second method including an air filter 22 located, in this aspect, at the media container 19. Any gas exchange method as is known can alternatively be utilized, however.

One skilled in the art will appreciate that one of the many benefits of the disclosed invention is the versatility of the system and cell modules. For example, in the bioreactor system illustrated in FIG. 3, the design attributes allow convenient and flexible reversal of the perfusion flow for a particular experimental protocol.

Figure 4:
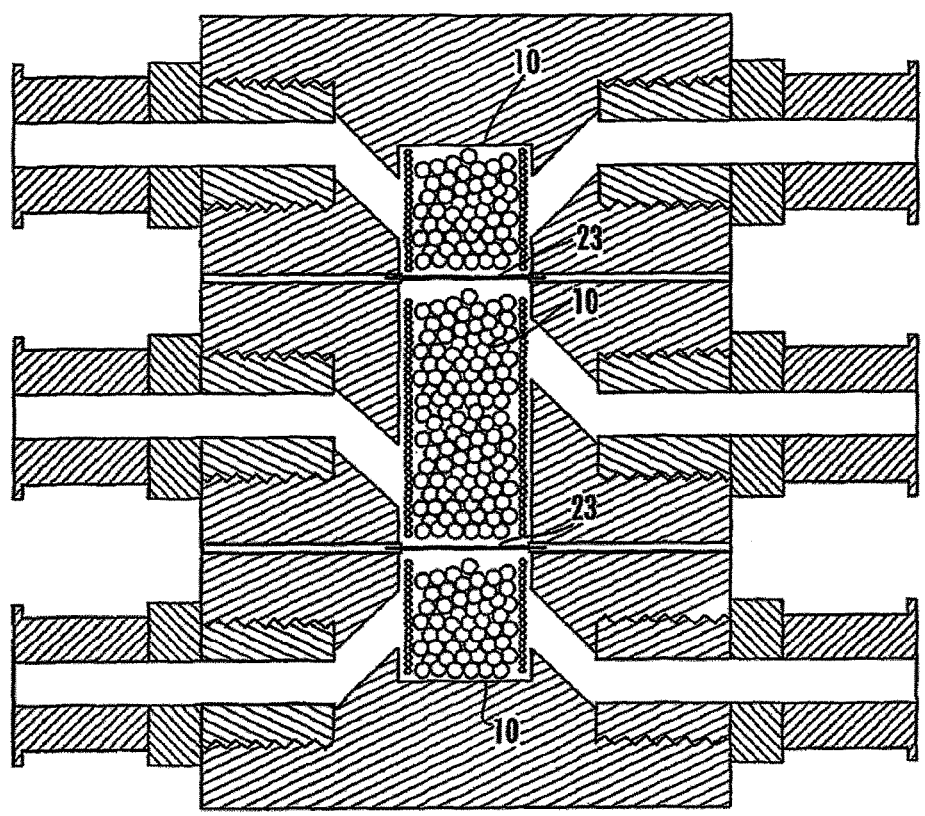
FIG. 4 is a schematic of a bioreactor system as herein disclosed including multiple cell culture chambers in biochemical communication with one another.

The bioreactor systems are not limited to single culture bioreactor systems or co-culture bioreactor systems in which only two independently controlled culture chambers are located adjacent to one another. In other aspects, additional cell modules can be selectively added to the bioreactor system such that a single culture chamber can be in selective biochemical communication with the contents of two or more other culture chambers. For example, a third chamber can house cells that can be in biochemical communication with the first culture chamber, optionally with a membrane separating the first and third chambers, though this aspect is not a requirement of the system such as for example in the instance stacked arrangement as illustrated in FIG. 4.

In one aspect, it is contemplated that the number of additional third chambers, which can be interior cell modules 12, which can be employed is not limited to a single interior cell module (i.e., three total cell modules 12 (one interior cell module and two end cell modules)), but can comprise 2, 3, 4, 5, 6, 7, 8, 9, 10 or more interior cell modules (i.e., 4, 5, 6, 7, 8, 9, 10, 11, 12, or more total cell modules 12, respectively). Thus, as a further embodiment disclosed herein are cell modules 12 that can be utilized as interior cell modules in a stacked configuration. Such interior cell modules 12 can comprise two top surfaces. Because the interior cell modules 12 comprise two top surfaces, the culture chamber 10 of these modules is open at both ends to allow for biochemical passage between the interior module and each of the exterior modules. As with the exterior cell modules, the top surface of the interior cell modules 12 can comprise means of sealingly engaging the top surface of other cell modules 12. Thus, it is contemplated herein that both of the top surfaces of the interior module 12 can comprise female fittings, male compression fittings, or a combination of both on each surface. Moreover, it is understood that the top surfaces of the interior cell module 12 can be identical or comprise an orientation with a male and a female end.

In another embodiment, one or more of the culture chambers of the system can be designed so as to provide the capability of subjecting the interior of the culture chamber to variable dynamic mechanical stimuli such as mechanical loading or variation in fluid flow through the culture chamber in order to vary the associated stress on the developing cells. Additionally one or more culture chambers of the system can be designed as to provide the capability of subjecting the interior of the culture chamber to electric current or a light source. Such an embodiment can be utilized to, for instance, trigger differentiation and development of stem cells contained in a culture chamber. In addition, cyclical hydrostatic loading patterns can be established, if desired, by simply cycling the pressurized fluid through the pressure chamber 24 through use of a solenoid valve and a time-delay relay, computer automation, or any other method that is generally known to one of ordinary skill in the art. Also, electrical currents can be provided through the use of an electrical probe in culture chamber of an adjacent cell module 12.

Figure 5:
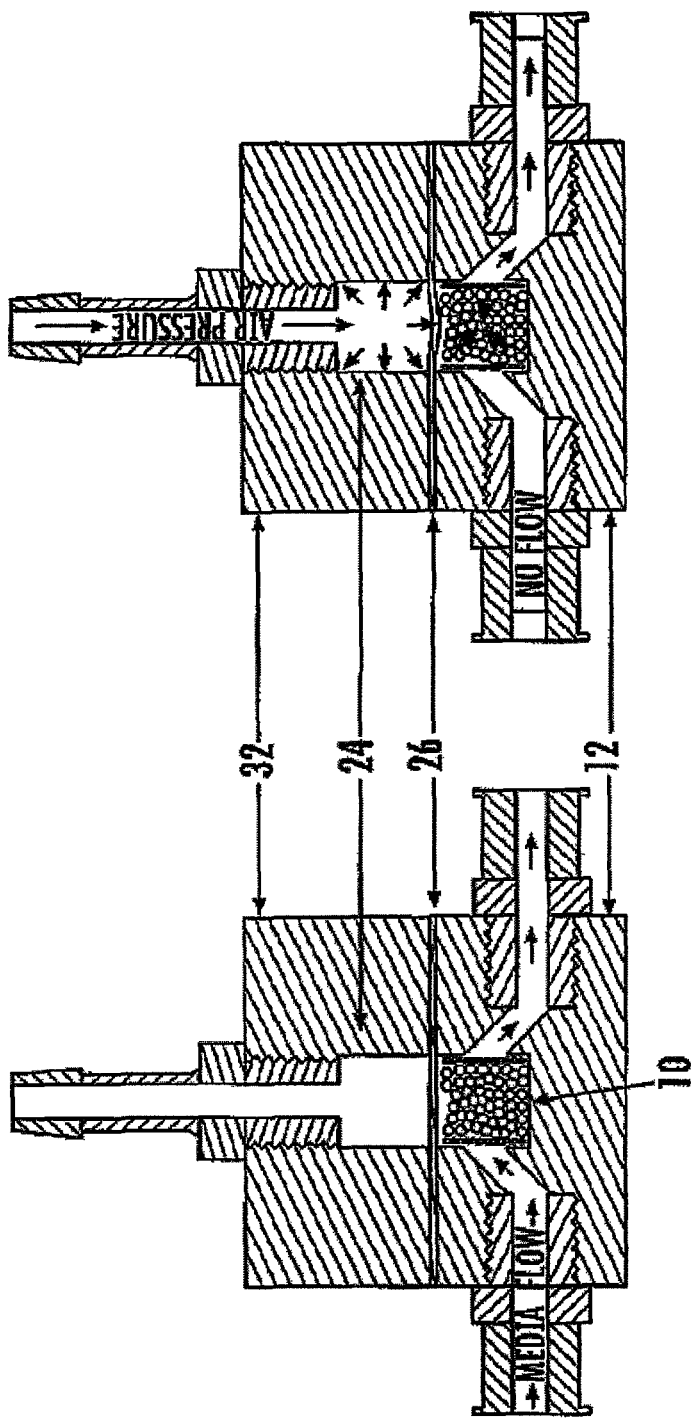
FIG. 5 illustrates another embodiment of the bioreactor system in which at least one of the cell modules of the bioreactor system can be subjected to periodic variation in hydrostatic pressure.

For example, according to one aspect, as illustrated in FIG. 5, a cell module 12 can be located immediately adjacent to a second cell module (not shown in FIG. 5), as described above. In addition, the cell module 12 can, on a second side of the module 12, be aligned with a pressure module 32 that can be utilized to vary the hydrostatic pressure on the contents of the culture chamber 10. According to this embodiment, the culture chamber 10 can be aligned with a pressure chamber 24 defined by pressure module 32, and the two adjacent chambers 10, 24 can be separated by an impermeable diaphragm 26. The introduction of pressurized fluid, e.g., air, into the pressure chamber 24, can deflect the diaphragm 26, as shown in FIG. 5B, and transfer the pressure to the volume of fluid in the culture chamber 10. In one embodiment, fluid flow through the culture chamber 10, as well as through other adjacent culture chambers, can be stopped prior to pressurizing the system, so as to develop a fixed volume of fluid within the affected portion of the system.

In another embodiment, each cell module can be designed to allow for the direct sampling and observation of the culture chamber such as optical and spectrophotometric analysis. Such designs can comprise but are not limited to optically transmissive culture chamber 10 such that the bottom of the well of the culture chamber comprises optical glass or plastic (i.e., a cell module comprising optically transmissible material). Thus, a microscope can directly visualize the culture chamber 10 by focusing through the optically transmissive culture chamber on the bottom side of the cell module 12. Additionally, high resolution and three-dimensional imaging modalities including, but not limited to, laser confocal microscopy, multiphoton microscopy, optical coherence tomography, and nuclear magnetic resonance can be used to visualize the cell culture. The cell module 12 can be made from opaque material, for example and without limitation, the cell module can be made from opaque white material for luminescent detection or opaque black material for fluorescent detection to effectively limit endogenous background signal. Additionally, the cell module 12 can comprise translucent, photoreactive, or optically filtering glass or polymers. For example, the cell module 12 can comprise a polymer that allows the passage of certain wavelengths of light or filters out ultraviolet light. Similarly, the culture chambers can comprise an inlet through which an analytical probe may be inserted.

It is understood that when sampling an observation of culture chamber is undertaken, it can be useful to provide a mechanism for securing the cell module 12 on any device used for observation such as a microscope or plate reader such as a spectrometer. Thus, disclosed herein are cell modules mounted in a microscope stage adaptor. Also disclosed are cell modules 12 mounted to well plate adaptor for use in instrumentation, i.e., spectrometer plate reader.

In yet another embodiment, an electrical current can be provided to the interior of a culture chamber 10 through the use of a piezoelectric membrane 23. The piezoelectric membrane upon compression generates an electric current which is supplied to the culture chamber. In an alternative aspect, the electric current can be supplied through the use of cell anchorage constructed with a piezoelectric material. For example, as pressure is applied through the introduction of a pressurized fluid, an electrical current is emitted from the cell anchorage. Alternatively, the bioreactor systems disclosed herein can comprise an electrically charging or piezoelectric scaffold.

In various aspects, multiple independent bioreactor systems can be provided that can incorporate various combinations of experimental stimuli, which can provide real time comparisons of the differing stimuli on the developing cellular constructs.

In a further aspect, a bank of multiple and identical systems can be established that can provide replication of a single experimental procedure and/or to provide larger cumulative amounts of the product cells that are grown, developed or otherwise produced within each of the individual culture chambers.

It is contemplated that the disclosed culture systems can be incorporated into a singular instrument to allow for the control of temperature, gas exchange, media contents and flow rate, external and mechanical stresses, and endpoint analysis. The instrumentation can comprise multiple modular components each designed to accomplish a specific task. Thus, for example, the disclosed instrumentation can comprise one or more of a means for seeding cells onto anchorages, a means for controlling the flow of media, a means for adding or changing media, a means for subjecting the culture to mechanical stress or pressure, an analytical probe, and a device for manipulating the parameters of the various modules as well as collecting and analyzing data (for example, a computer and a computer program designed to accomplish these tasks).

The culture systems disclosed herein have many uses known to those of skill in the art. For example, the disclosed culture systems and cell modules can be used in tissue engineering where a 3D bioreactor is useful to properly model tissue.

In a further aspect, it is contemplated that for tissue passaging, a material composition comprising two or more materials can be used. In one example, the material composition can comprise a stiff culture material having substantially large porosity, such as, for example and without limitation, having pores of average size between 50 µm and 2 mm, into which a soft culture material has been introduced. "Stiff culture material" is defined herein as tissue culture material having a tensile elastic modulus, or Young's modulus, of about 1 GPa or greater and "soft culture material is defined as tissue culture material having a tensile elastic modulus, or Young's modulus, of about 500 MPa or less. In one example, and without limitation, the stiff culture material can be formed from metal, synthetic polymer, ceramic and the like. In one example, and without limitation, the soft culture material can be formed from a polymer of biological origin, a synthetic polymer, or a combination of biological and synthetic polymers. The soft culture material may then be formed as a hydrogel or an uncrosslinked oligomers of polymers either synthetic or of natural origin, and the like.

It is understood that as the bioreactor systems disclosed herein are utilized for passaging cells in culture, that in one aspect, the disclosed bioreactor systems comprise cells. It is further understood that the cells attach to the culture material. Thus, in one aspect, disclosed herein are bioreactor systems further comprising cells attached to the culture material. In one aspect, the cells are attached to the soft culture material. The cells can be introduced to the soft culture material before or after introduction of the soft culture material to the stiff culture material. Thus, in one aspect, the cells are introduced to the soft culture material and with the soft culture material introduced to the stiff culture material. For example, the cells can be encapsulated in a hydrogel soft culture material and then introduced to the stiff culture material.

In one aspect, the soft culture material can be configured or otherwise have a means for releasing the soft material from the stiff culture material. In one exemplary aspect, the releasing means can comprise chemical degradation or other change initiated by light, temperature, pH, chemical catalyst, and the like.

In another aspect, the material composition may further comprise a biocompatible aqueous solvent such as, for example and without limitation, Minimum Essential Medium (MEM), developed by Harry Eagle, and its many altered forms. In this aspect, it is contemplated that the biocompatible aqueous solvent can provide the basic benefits of cell culture media, which include, without limitation, provision of nutrients and removal of cell waste.

Further, in addition to the usual or conventional soluble factors known to be generally beneficial for the sustained culture of cells, such as, for example and without limitation, Inorganic Salts: CaCl2 (anhydrous), Fe(NO3)3.9H2O, MgSO4 (anhydrous), KCl, NaHCO3, NaCl, NaH2PO4.H2O; Amino Acids: L-Alanine, L-Arginine.HCl, L-Asparagine.H2O, L-Aspartic Acid, L-Cysteine.HCl, L-Cystine.2HCl, L-Glutamic Acid, L-Glutamine, Glycine, L-Histidine.HCl.H2O, L-Isoleucine, L-Leucine, L-Lysine-.HCl, L-Methionine, L-Phenylalanine, L-Proline, L-Serine, L-Threonine, L-Tryptophan, L-Tyrosine.2Na.2H2O, L-Valine; Vitamins: L-Ascorbic Acid.Na, D-Biotin, Choline Chloride, Folic Acid, myo-Inositol, Lipoic Acid, Nicotinamide, D-Pantothenic Acid, (hemicalcium), Pyridoxine.HCl, Riboflavin, Thiamine.HCl; Other: Adenosine, Cytidine, 2'-Deoxyadenosine, 2'-Deoxycytidine.HCl, 2'-Deoxyguanosine, D-Glucose, Glutathione (reduced), HEPES, Phenol Red (Sodium Salt), Pyruvic Acid, Sodium Pyruvate, Thioctic Acid, Thymidine, Uridine, and the like, the aqueous solvent can provide specific soluble factors and/or stimulants which are known to affect, e.g., either increase, decrease or stabilize, cell proliferation within the exemplary stiff/soft material composition. In another aspect, the aqueous solvent may comprise oligomers or fragments of the soft material that are known to effect cell attachment to the soft material originally contained within the stiff culture material, such as, for example and without limitation, natural materials common to mammalian tissue such as collagen, chondroitin sulfate, fibrin, fibrinogen, glycosaminoglycan, hyaluronic acid, keratin, laminin, or thrombin; natural materials common to non-mammalian tissue or derived from non-mammalian organisms such as chitin, chitosan, dextran, starches or other polysaccharides, gelatin, silks, or synthetic materials such as HEMA/hydroxyethyl methacrylate, PCL/poly(e-caprolactone), PEG/poly(ethylene glycol), PEMA/poly(ethyl methacrylate), PEO/poly(ethylene oxide), PEVA/poly(ethylene-vinyl alcohol), PGA/poly(glycolide), PHEMA/poly(hydroxyethyl methacrylate), PLA/poly(lactide), PLG/poly(L-lactide-glycolide), PLGA/poly(lactic-co-glycolic acid), PLL/poly-l-lysine, PLLA/poly(L-lactic acid), PVA/Polyvinyl alcohol and the like.

Optionally, the material composition can comprise a stiff tissue culture material in the physical form of discrete beads or microparticles to or within which a soft culture material has been introduced. In one example, and without limitation, the stiff culture material can be formed from metal, synthetic polymer, ceramic and the like. In one example, and without limitation, the soft culture material can be in the physical form of a hydrogel or uncrosslinked oligomers of polymers either synthetic or of natural origin, and the like. In one example, and without limitation, the soft culture material can be formed from polymers of biological origin, synthetic polymers, or combinations of synthetic and biological polymers. As one skilled in the art will appreciate, aside from this physical change in the initial physical form of the stiff culture material, the material composition of this exemplary aspect has the same properties and behavior as the aspect previously disclosed.

In yet another aspect, a method of 3D cell passaging is provided that comprises providing a population of cells to be passaged and introducing the population of cells into the material composition, that is comprised of the combination of stiff and soft tissue cultural materials. In this method, it is contemplated that at least a portion of the population of cells will attach to at least portions of the soft culture material. It is further contemplated that the cells can attach prior to or after introduction of the soft culture material to the stiff culture material. For example, the cells can be encapsulated into a soft culture material such as a hydrogel and thereafter introduced to the stiff culture material. In one aspect, it is further contemplated that the "attached" population of cells can be cultured under conditions that are typical for the growth of the respective cells, i.e., using appropriate temperature, humidity, and/or gas exchange. At a desirable and or predetermined time after the cells attachment, the method can further comprise causing the soft culture material to disassociate from the stiff culture material, thereby releasing the soft culture material and the cells from the stiff culture material of the material composition. In another aspect, the method can further comprise dividing the recovered cells, with or without remnants of the soft culture material, into multiple populations and repeating the method using the subdivided populations. It is of course contemplated that this exemplary process can be done recursively.

In one exemplary aspect of the method of 3D cell passaging, the at least one cell module can be preloaded with a predetermined quantity of material composition, such as, the exemplary stiff/soft culture material composition. It is contemplated that the material composition can fill between about 5 and 100% of the available space in the cell culture chamber. For example and without limitation, in a configuration having a cell culture chamber with a 250 μL volume, a material composition of between 12.5 μL and 250 μL can be utilized. It is also contemplated that the exemplary stiff/soft culture material composition can have multiple configurations to include, without limitation, providing a material composition that allows for a 3D environment within the at least one cell module of appropriate desired density and surface area to support growth of the particular cells being cultured. Therefore, it is contemplated that the matrix has the surface area to allow for attachment of the cells as well as the surface area to allow for proliferation of the cells and flow through of any growth factors, nutrients, media, environmental factors, chemokines, chemicals, cytokines, and the like to which it is desired the cells be exposed. Optionally it is contemplated that the exemplary stiff/soft culture material composition can provide a material composition that allows for a 3D environment within the at least one cell module of appropriate desired density, in which the matrix upon which the population of cells attaches has less free space if it is desirable to maintain a stable cell population rather than proliferating the cell population.

Subsequently, an operator can couple the at least one cell module into the bioreactor flow circuit and introduce the population of cells into the at least one cell module. After introduction of the cells and the attachment to the soft culture material of the material composition, the cells can then be cultured in the at least one cell module for a desired and or predetermined period of time to effect either doubling or maintenance of the introduced population of cells. It is contemplated that, during the culture process, the operator can affect cell behavior (e.g. differentiation, growth, metabolite, vector production, and the like) by using media containing specific soluble factors, such as, for example and without limitation, inorganic salts, amino acids, vitamins, ribonucleosides, deoxyribonucleosides, and the like, that can encourage a desired outcome.

Upon the desired and or predetermined period of time expiring, the operator can introduce a trigger or stimulus designed to disassociate the soft culture material from the stiff culture material of the material composition. In this aspect, the soft culture material can be configured or otherwise have a means for releasing the soft culture material from the stiff culture material. In one exemplary aspect, the releasing means can comprise chemical degradation or other change initiated by light, temperature, pH, chemical catalyst, and the like. Therefore, it is contemplated that the operator triggered stimulus can comprise, without limitation, chemical stimuli, i.e., introduced into media supplied to the at least one cell module, pH stimuli, thermal stimuli, i.e., for soft culture material of the material composition configured to fall apart or otherwise degrade upon increase or decrease in temperature, light stimuli, and like stimuli. Next, the operator can collect cells and soft culture material fragments downstream of the at least one cell module. Optionally, the operator can separate the cells from the soft material fragments or can allow the cells and the soft culture materials to remain unseparated.

Optionally, it is contemplated that the collected cells can, if desired, comprise cells that can be divided to form a plurality of "new" populations of cells that can be subsequently individually introduced into separate cell modules that are preloaded with the material composition, such as, for example, the exemplary soft/stiff material composition. It is contemplated that the "new" population(s) of cells can be introduced into/onto the soft culture material prior to introduction of the soft culture material to the stiff culture material. For example, the "new" population(s) of cells can be encapsulated in a soft culture material such as a hydrogel.

It is contemplated that at least portions of the material composition can be recycled. For example, if the stiff culture material forming a portion of the material composition is valuable, e.g., a metal, the spent cell module can be recycled. In one non-limiting example, it is contemplated that the stiff culture scaffold of the material composition could be recovered from the spent cell module, cleansed, and then subsequently preloaded into a cell module for future use.

EXAMPLES

3D Cell Passaging Experiment

Herein provides an example of a method by which cells are cultured in vitro, expanded, released from a 3D soft-stiff composite scaffold via digestion and captured (passaged) for purposes of reseeding into additional 3D culture vessels. This method removes the need to culture the cells in traditional two-dimensional (2D) conditions such as Petri dishes and well plates, which has been shown to result in non-physiologically relevant cell response and function. Additionally, 3D passaging permits the continuous culture of cells in a closed system over longer durations while maintaining the cells' natural phenotype and function.

Materials and Methods

Culture Chamber: 3DKUBE™ 3D Cell Culture Plasticware—Independent Chambers Configuration (KIYATEC Inc., Pendleton, S.C.)

Scaffold: A soft-stiff composite scaffold was fabricated consisting of "stiff" polystyrene (PS) struts with interconnected porosity and "soft" hyaluronic acid (HA) hydrogel filling the interconnected porosity. The PS porous scaffold consisted of a stacked crosshatch of 300 μm diameter fibers forming an average 400 μm pore size. Overall dimensions of the PS porous scaffold were 5 mm in diameter and 1.8 mm in thickness. The PS scaffold was placed in the bottom of a well of a 96-well plate. A volume of 50 μL of methacrylated HA at 2% w/v including 12959 photoinitiator was pipetted into the porosity of the PS scaffold. The HA was crosslinked for 6.5 minutes at approximately 10 mW/cm$^2$. The well plate was incubated at 37° C. and 95% RH for one hour to further crosslink the "soft" HA hydrogel within the porosity of the "stiff" PS scaffold. The entire soft-stiff composite scaffold was frozen for two hours followed by overnight lyophilization to create porosity in and around the contracted HA hydrogel and PS struts.

Cells: SHEP (human neuroblastoma) cell line transfected with a luciferase expressing gene (SHEP-Luc)

Results and Discussion

The soft-stiff composite scaffold was stored under vacuum at 20° F. to prevent rehydration of the lyophilized HA hydrogel component. Upon commencing the study, a single soft-stiff (HA-PS) scaffold was placed in the culture chamber of a special white opaque 3DKUBE Independent Chambers configuration. The inlet and outlet ports of the 3DKUBE were capped with standard male luer plugs. Prior to assembling the 3DKUBE modules, the soft-stiff scaffold was seeded with a 100 µL cell suspension of SHEP-Luc cells (1.0E+5) in Dulbecco's Modified Eagle Medium (DMEM) supplemented with 10% fetal bovine serum (FBS) and 1% penicillin-streptomycin. Seeding was done by pipetting the cell suspension directly onto the soft-stiff scaffold, covering the open 3D culture chamber in a 60 mm plastic culture dish and allowing cell attachment under static conditions for two hours. Following the two hour static period, the remaining seeding medium was gently removed and the complete 3DKUBE was assembled and connected to the syringe pump flow circuit consisting of a 10 mL syringe, platinum-cured silicone tubing, standard luer connectors and a gas exchange reservoir bag. The complete flow circuit, including the assembled 3DKUBE, was primed slowly by hand and connected to the syringe pump to commence 50 µL/min volumetric flow rate. A total of 10 mL of DMEM was used for the duration of the 5 day experiment.

Samples were prepared and evaluated via Hoechst 33258 dye at time points of Day 2 and Day 5. Upon completion of the respective culture period (two or five days), a 3 mL syringe was used to manually inject 500 µL of 40 units/mL hyaluronidase digestion solution (608 units/mg hyaluronidase) in PBS into the 3D culture chamber via the luer port. Following slow perfusion of the digestion solution into the 3D culture chamber, the system was incubated under periodic agitation (manual infusion and withdrawal) for 4 hours to digest the "soft" HA portion of the soft-stiff composite scaffold. Following digestion, the contents of the 3D culture chamber (i.e., the dissociated cells and soft culture material) were gently drawn off into the 3 mL syringe to model the concept of 3D cell passaging. The stiff culture material remained in the culture chamber. The resulting cell suspension of cells and soft culture material was placed in a microcentrifuge tube and spun down to collect the cell pellet. The cell pellet was stored dry at −80° C. followed by Hoechst 33258 dye evaluation to quantify the seeding efficiency. A range of known cell quantities were cultured, frozen and evaluated in parallel with experimental samples to provide a correlative standard curve for conversion of fluorescent units to cell number.

Samples were resuspended in 400 µL ddH2O and incubated for one hour at 37° C. followed by storage again at −80° C. and then thawed to room temperature. A volume of 100 µL of each sample were transferred (in duplicate) to a black, clear bottom 96-well plate. 100 µl of Hoechst Reagent (Invitrogen FluoReporter Blue Fluorometric dsDNA Quantification Kit) was then added to each well before reading the fluorescence using a Wallac Victor$^2$ 1420 fluorescent plate reader with a 355 nm excitation filter and a 460 nm emission filter.

Figure 6:
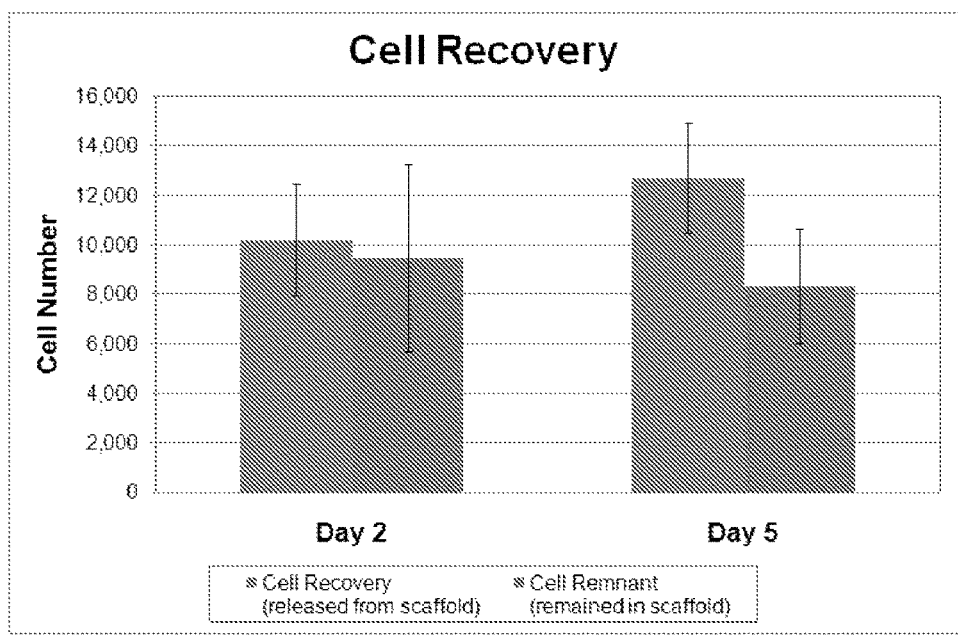
FIG. 6 shows Hoechst 33258 dye Day 2 and Day 5 endpoint evaluation of cell quantity that was recovered (Cell Recovery) following digestion of the "soft" HA hydrogel scaffold as well as cell quantity that remained (Cell Remnant) in the scaffold after the 4 hour digestion procedure.

The 3D culture demonstrated an increasing numerical trend from Day 2 to Day 5 of the study (FIG. 6). Cells were successfully recovered from the 3D soft-stiff composite scaffold via digestion and perfusion via the luer ports. Additional cells were found to remain within the "soft" HA scaffold following the 4 hour digestion procedure suggesting a recommended increase in the digestion period to recover more cells. Ultimately, the study provides a relevant example of 3D cell passaging using the 3DKUBE™ 3D Cell Culture Plasticware in combination with a soft-stiff composite scaffold useful to the art of cell and tissue culture.

What is claimed is:

1. A bioreactor system for 3D passaging of cells comprising;
   at least one cell module defining a first cell culture chamber, an inlet, an outlet, and a port opening, wherein the port opening is on one end of the cell culture chamber; and
   a scaffold, located within the at least one cell module, comprising a stacked crosshatch of struts or fibers defining the pores of the scaffold, and a cell anchorage deposited within the pores of the scaffold, wherein cells attach to the cell anchorage.

2. The bioreactor system of claim 1, wherein the scaffold has a porosity between 50 µm and 2 mm.

3. The bioreactor system of claim 1, wherein the struts or fibers are made from metal, ceramic, glass, or polymers.

4. The bioreactor system of claim 1, wherein the cell anchorage comprises a polymer selected from the group consisting of polylactide, chondroitin sulfate, polyesters, polyethylene glycols, polycarbonates, polyvinyl alcohols, polyamides, polyacrylamides, poly methacrylate, polyether esters, polyurethanes, polycaprolactone, polvphosphazenes, polyorthoesters, polyglycolide, copolymers of lysine and lactic acid, copolymers of lysine-RGD lactic acid, chitosan, agarose, alginate, collagen, hyaluronic acid, carrageenan, demineralized bone matrix, or a combination thereof.

5. The bioreactor system of claim 4, further comprising a cell encapsulated in a hydrogel.

6. The bioreactor system of claim 1, wherein the cell anchorage is released from the scaffold by chemical degradation, light exposure, change in temperature, change in pH, or exposure to a chemical catalyst.

7. The bioreactor system of claim 1, wherein the cell anchorage is introduced into or onto the scaffold prior to being loaded into the bioreactor system.

8. The bioreactor system of claim 7, wherein a cell is encapsulated in the cell anchorage prior to introduction to the scaffold.

9. The bioreactor system of claim 1, wherein the cell anchorage is introduced into the scaffold after the scaffold is loaded into the bioreactor system.

10. A method of 3D cell passaging in a bioreactor system, comprising:
    providing a population of cells to be passaged; and
    introducing the population of cells into a bioreactor system comprising a scaffold, the scaffold comprising a stacked crosshatch of struts or fibers defining pores in the scaffold, and a cell anchorage deposited within the pores of the scaffold, wherein the cells attach to the cell anchorage.

11. The method of claim 10, wherein the cells are introduced into the cell anchorage prior to introduction of the cell anchorage to the struts or fibers.

12. The method of claim 10, further comprising causing the cell anchorage to disassociate from the stiff struts or fibers.

13. The method of claim 12, further comprising isolating the cells and cell anchorage from the bioreactor system.

14. The method of claim 12, further comprising recovering dissociated cells and dividing the cells into multiple populations.

15. The method of claim 14, further comprising introducing one or more divided cells into a second bioreactor system.

16. The method of claim 15, wherein the second bioreactor system comprises a second scaffold, the second scaffold comprising a stacked crosshatch of struts or fibers defining pores in the scaffold, and a cell anchorage that is deposited within the pores of the second scaffold.

17. The method of claim 16, wherein the cells are introduced into the cell anchorage prior to introduction of the cell anchorage into the pores of the second scaffold.

18. The bioreactor system of claim 1, wherein the cell anchorage has a Young's modulus of about 500 MPa or less.

* * * * *

UNITED STATES PATENT AND TRADEMARK OFFICE
CERTIFICATE OF CORRECTION

PATENT NO. : 10,240,121 B2
APPLICATION NO. : 13/817636
DATED : March 26, 2019
INVENTOR(S) : Matthew R. Gevaert et al.

Page 1 of 1

It is certified that error appears in the above-identified patent and that said Letters Patent is hereby corrected as shown below:

On the Title Page

Item (73), Line 3: "Pendleton, SC" should read -- Greenville, SC --

Signed and Sealed this
Seventh Day of May, 2019

Andrei Iancu
*Director of the United States Patent and Trademark Office*